United States Patent [19]

Misch

[11] 4,408,990
[45] Oct. 11, 1983

[54] ENDODONTIC DENTAL IMPLANT

[76] Inventor: Carl E. Misch, 3646 S. Elder, West Bloomfield, Mich. 48033

[21] Appl. No.: 372,080

[22] Filed: Apr. 26, 1982

[51] Int. Cl.³ .............................................. A61C 5/08
[52] U.S. Cl. .................................... 433/224; 433/220
[58] Field of Search ................ 433/224, 220, 233, 174

[56] References Cited

U.S. PATENT DOCUMENTS

| 3,499,222 | 3/1970 | Linkow et al. | 32/2 |
|---|---|---|---|
| 3,813,779 | 6/1974 | Tosti | 433/224 |
| 4,084,318 | 4/1978 | McEachem | 433/174 |
| 4,103,422 | 8/1978 | Weiss et al. | 32/10 A |
| 4,175,565 | 11/1979 | Chiarenza et al. | 433/32 |

Primary Examiner—Robert Peshock
Attorney, Agent, or Firm—Basile, Weintraub & Hanlon

[57] ABSTRACT

An endodontic implant for insertion into the jawbone of a patient through a bore formed in a tooth to stabilize the tooth. The implant comprises an elongated post having sides tapering inward from a larger diameter first end to a smaller diameter second end. A plurality of external threads are formed on the post and extend along the length of the post from the first and second ends for a predetermined distance. An intermediate, tapered, smooth-sided section is formed on the post between the first and second threaded portions.

2 Claims, 2 Drawing Figures

ENDODONTIC DENTAL IMPLANT

BACKGROUND OF THE INVENTION

1. Field of the Invention

This invention relates, in general, to dental implants and, more specifically, to endodontic dental implants for insertion into the jawbone of a patient through a bore formed in a tooth to stabilize the tooth.

2. Description of the Prior Art

Endodontic implants or stabilizers have been extensively used to stabilize teeth which have been weakened or loosened due to injury or root disease. Such endodontic implants or stabilizers typically come in two forms—a smooth tapered pin or a threaded, self-tapping pin.

The smooth tapered pin is wedged into a bore formed in the tooth and held in place by a dental cement. This type of dental implant, however, has experienced problems relating to a lack of resistance to withdrawal from the tooth, the formation of a complete apical seal at the apex of the tooth and a poor implant-bone relationship.

The threaded, self-tapping implant, such as that disclosed in U.S. Pat. No. 4,103,422, is formed with threads along the length thereof which engage the sides of the bore within the tooth to form a mechanical seal with the tooth which provides greater implant retention. However, such threaded, self-tapping implants are not without their problems. In using such implants, a bore is initially drilled in the tooth which has the same diameter along its entire length. As the implant is threaded into the bore, the threads engage the sides of the bore along its entire length. At the lower portions of the tooth which have narrowing side walls of reduced thickness, the mechanical force exerted by the threads of the implant on the tooth can cause cracking of the tooth. In addition, due to the presence of the threads along the entire length of the implant, it is difficult to ensure that a complete seal is formed at the lower end of the bore at the apex of the tooth. Furthermore, since this type of implant has a constant diameter along its length, if the bore in the tooth is too large, there is no way to adhere the implant to the tooth or ensure an apical seal. This lack of a complete apical seal commonly leads to failure of the implant in securely retaining the tooth in the jawbone of the patient.

Thus, it would be desirable to provide an endodontic implant which overcomes the problems of the previously devised dental implants. It would also be desirable to provide an endodontic implant which enables a complete apical seal to be formed at the apex of the tooth. Finally, it would be desirable to provide an endodontic dental implant which is formed to exert minimal forces at the lower, narrower regions of the tooth so as to prevent cracking of the tooth in this area.

SUMMARY OF THE INVENTION

There is disclosed herein a new and improved endodontic dental implant suitable for insertion to the jawbone of a patient through a bore formed in a tooth. The implant comprises an elongated post having first and second ends. The sides of the posts taper inward along its length from a larger diameter first end to a smaller diameter second end. A plurality of external threads are formed on the post adjacent the first end and extend a predetermined distance along the post from the first end to define a first threaded section. A plurality of external threads are formed on the post adjacent the second end and extend a predetermined distance along the post from the second end to define a second threaded section. The first and second threaded sections are spaced apart to define an intermediate, tapered, smooth-sided section on the post.

The endodontic implant of the present invention overcomes many of the problems encountered with the use of previously devised dental implants. Due to the formation of an intermediate, tapered, smooth-sided section between two threaded sections on the post, the formation of cracks in the tooth adjacent the apex of the tooth which are typically caused by the mechanical forces exerted by the threads of previously devised implants on the tooth are eliminated. Furthermore, the smooth intermediate section enables a complete apical seal to be more easily formed at the apex of the tooth which eliminates subsequent failure of the implant in retaining the tooth securely in position in the jawbone of the patient. In addition, the first threaded section forms a secure implant-tooth relationship in the thicker portion of the tooth and the second threaded section provides a secure implant-bone relationship.

BRIEF DESCRIPTION OF THE DRAWING

The various features, advantages and other uses of the present invention will become more apparent by referring to the following detailed description and drawing in which.

DESCRIPTION OF THE PREFERRED EMBODIMENT

Figures 1, 2:
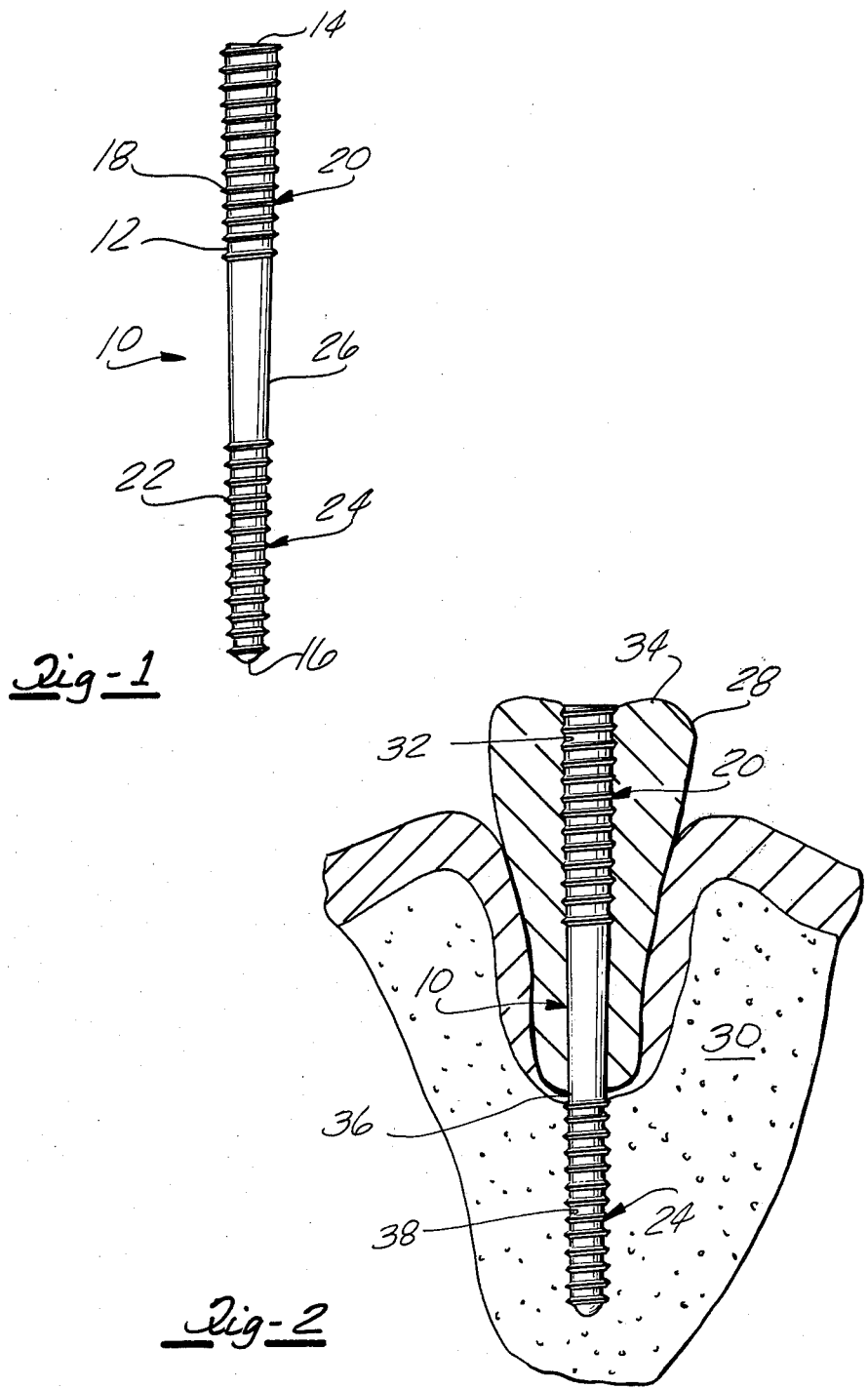
FIG. 1 is an elevational view of an endodontic implant constructed in accordance with the teachings of the present invention.
FIG. 2 is a cross sectional view showing the position of the implant of the present invention after it has been inserted through a tooth into the jawbone of a patient.

Throughout the following description and drawing, identical reference numbers are used to refer to the same component shown in multiple figures of the drawing.

Referring now to the drawing, and in particular to FIG. 1, there is shown an endodontic implant 10 constructed in accordance with the teachings of the present invention. The endodontic implant 10 is adapted for use in stabilizing a tooth by insertion through a bore formed in the tooth into the jawbone of a patient.

The implant 10 comprises an elongated post-like member 12 having opposed first and second ends 14 and 16, respectively. The post 12 may be formed of any material which is suitable for use in an oral environment. Preferably, a biocompatible metallic material is used such as, titanium or vitallium.

As noted above, the implant 10 is provided with first and second ends 14 and 16. Although the first or upper end 14 is illustrated as having a flat surface, it should be noted that the implant 10 is initially provided with a handle means, not shown, which is used for threading the implant into the tooth and is then cut off and disgarded. As shown in FIG. 1, the implant 10 has a generally cone-shaped configuration formed by side walls which taper inwardly from the larger diameter first end 14 to the smaller diameter second end 16. Preferably, the side walls of the implant 10 taper gradually and continuously inward over the entire length of the post member 12.

Although the length of the implant 10 remains constant, the overall cross-section of the implant 10 may be provided in several sizes to accommodate use of the implant 10 in different size teeth. Preferably, the diameter of the first end 14 of the implant 10 is chosen to correspond with the diameter of conventional #70, #90 and #120 size dental reamers.

The dental implant 10 of the present invention is provided with external threads disposed in two spaced sections along the length of the post 12. A plurality of external threads 18 are formed adjacent the first end 14 of the post member 12 and extend for a predetermined distance along the post member 12 from the first end 14 to define a first threaded section 20. Although the threads 18 are illustrated as being formed in a continuous spiral around the post 12, it will be understood that other types of threads, such as discontinuous tapping-type threads, may also be employed on the dental implant 10 of the present invention. Further, it is preferred that the threads 18 forming the first threaded section 20 on the implant 10 extend for approximately 10 mm. from the first end 14 of the post member 12.

A plurality of external threads 22 are similarly formed on the post member 12 adjacent the second end 16 and extend for a predetermined distance along the post member 12 from the second end 16 to form a second threaded section 24. The threads 22 are formed in the same manner as the threads 18 in the first threaded section 20 and, preferably, extend for approximately 10 mm. from the second end 16.

The first and second threaded portions 20 and 24, respectively, are spaced apart on the post member 12 and define an intermediate smooth-sided section 26.

The function of the tapered side walls, threaded sections 20 and 24 and smooth-sided intermediate section 26 will become more apparent by referring to FIG. 2 which illustrates the position of the dental implant 10 after it has been inserted through a tooth 28 into the unerlying jawbone 30 of a patient. The dental implant 10 of the present invention is adapted to be inserted through a bore 32 formed in the tooth 28 and jawbone 30 of the patient. The bore 32 extends vertically from the crown 34 through the apex 36 of the tooth 28 into the jawbone 30 of the patient.

Preferably, the portion of the bore 32 within the tooth 28 is formed with converging tapered side walls which are formed by successively applying a series of increasing diameter dental reamers which are inserted into the bore 32. A drill is then inserted through the bore 32 and is used to form the lower portion 38 of the bore 32 in the jawbone 30 of the patient.

An endodontic cement is applied at the exit end of the implant 10 and a suitable dental adhesive, such as polycarboxylate cement, is applied to the balance of the implant 10 on the intraroot portion. The cement adheres to the dentin within the tooth 28 and fills any voids that may exist within the tooth.

The implant 10 is then inserted into the bore 32 within the tooth 28 and the jawbone 30 by slowly rotating it until it is fully seated within the bore 32. The handle at the upper or first end 14 of the implant 10 is then cut off and disgarded. In this manner, the implant 10 is secured to the tooth 28 and jawbone 30 by the mechanical forces exerted by the threads and the polycarboxylate cement.

Furthermore, the second threaded section 24 extends only for a predetermined length along the post member 12, as noted above. This length corresponds to the length of the lower portion 38 of the bore 32 such that only the smooth sided section 26 on the implant 10 will be located at the apex 36 of the tooth 28. This enables a complete apical seal to be formed at the apex of the tooth 28 which prevents subsequent failure of the implant 10. In addition, due to the tapering side walls of the implant 10, the largest diameter of the second threaded section 24 is less then the diameter of the bore 32 at the apex 36 of the tooth 28 so as to enable the second threaded section 24 to pass through the lower end of the bore 32 without contacting the side walls of the bore 32 in the tooth 28. This prevents any mechanical forces from being exerted on the narrower regions of the tooth 28 which could lead to cracking of the tooth 28 in these areas.

What is claimed is:

1. An endodontic implant for insertion through a tooth into the jaw bone of a user comprising:
   an elongated post having first and second opposed ends;
   the sides of the post tapering inward along the length of the post from a larger diameter first end to a smaller diameter second end;
   a plurality of external threads formed on the post adjacent the first end and extending a predetermined distance along the post from the first end to define a first threaded section;
   a plurality of external threads formed on the post adjacent the second end and extending a predetermined distance along the post from the second end to define a second threaded section; and
   the first and second threaded sections being spaced apart to define an intermediate, tapered, smooth-sided section on the post;
   the lengths of the first and second threaded sections being selected so as to locate the intermediate smooth-sided section within the narrow apex region of the tooth.

2. The endodontic implant of claim 1 wherein:
   the first threaded section extends for approximately 10 mm. along the length of the post;
   the intermediate section extends for approximately 12 mm. along the length of the post; and
   the second threaded section extends for approximately 10 mm. along the length of the post.

* * * * *